United States Patent
Hsieh

(10) Patent No.: US 10,393,631 B2
(45) Date of Patent: Aug. 27, 2019

(54) SIMPLIFIED EXTRACTION METHODS FOR THE RAPID DETERMINATION OF SPECIES CONTENT OF ADIPOSE TISSUE BASED ON THE DETECTION OF TNI IN IMMUNOASSAYS

(71) Applicant: FLORIDA STATE UNIVERSITY RESEARCH FOUNDATION, INC., Tallahassee, FL (US)

(72) Inventor: Yun-Hwa Peggy Hsieh, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 701 days.

(21) Appl. No.: 14/927,956

(22) Filed: Oct. 30, 2015

(65) Prior Publication Data

US 2016/0047806 A1 Feb. 18, 2016

Related U.S. Application Data

(62) Division of application No. 14/421,626, filed as application No. PCT/IB2013/058019 on Aug. 27, 2013, now abandoned.

(60) Provisional application No. 61/693,811, filed on Aug. 28, 2012.

(51) Int. Cl.
   *G01N 1/28* (2006.01)
   *C07K 1/14* (2006.01)
   *G01N 33/68* (2006.01)

(52) U.S. Cl.
   CPC .............. *G01N 1/28* (2013.01); *C07K 1/145* (2013.01); *G01N 33/68* (2013.01)

(58) Field of Classification Search
   None
   See application file for complete search history.

(56) References Cited

U.S. PATENT DOCUMENTS

| | | | |
|---|---|---|---|
| 4,208,323 A | 6/1980 | Murray | |
| 5,178,834 A | 1/1993 | Kagayama et al. | |
| 5,384,149 A * | 1/1995 | Lin .................. | A23J 1/002 426/417 |
| 6,005,076 A | 12/1999 | Murray | |
| 7,207,010 B2 | 4/2007 | Hirneisen et al. | |
| 7,297,500 B2 * | 11/2007 | Hsieh ................ | C07K 16/18 435/1.1 |
| 2003/0022248 A1 | 1/2003 | Hsieh et al. | |
| 2004/0010122 A1 * | 1/2004 | Nnanna ............. | A23J 1/10 530/356 |
| 2005/0058756 A1 | 3/2005 | Green | |
| 2006/0292558 A1 * | 12/2006 | O'Neill ............ | B01L 3/502715 435/5 |
| 2010/0249378 A1 | 9/2010 | Wanasundara et al. | |
| 2012/0171345 A1 | 7/2012 | Kelleher et al. | |

OTHER PUBLICATIONS

Celis et al., Identification of Extracellular and Intracellular Signaling Components of the Mammary Adipose Tissue and Its Interstitial Fluid in High Risk Breast Cancer Patients, Molecular & Cellular Proteomics, 4, 2005, 492-522 (Year: 2005).*
Kotura et al., Establishment of a sandwich ELISA for the determination of beef content in processed foods by using monoclonal antibodies to myoglobin, 23(3) Food and Agricultural Immunology 2012, 289-301. (Year: 2012).*
P. Trayhurn, C. A. Drevon and J. Eckel, "Secreted proteins from adipose tissue and skeletal muscle—adipokines, myokines and adipose/muscle cross-talk," Arch. Physiol. Biochem. 117(2):47-56 (2011).
L. Vaclavik, V. Hrbek, T. Cajka, B.A. Rohlik, P. Pipek, and J. Hajslova, "Authentication of animal fats using direct analysis in real time (DART) ionization-mass spectrometry and chemometric tools," J. Agric. Food Chem. 59(11):5919-26 (2011).
J.M. Wilkinson and R.J. Grand, "Comparison of amino acid sequence of troponin I from different striated muscles," Nature 271(5640):31-35 (1978).
J.D. Wood, R.I. Richardson, G.R. Nute, A. V. Fisher, M.M. Campo, E. Kasapidou, P.R. Sheard, and M. Enser, "Effects of fatty acids on meat quality: a review," Meat Sci. 66(1):21-32 (2004).
H. Yang, Z.Y. Xu, M.G. Lei, F.E. Li, C.Y. Deng, Y.Z. Xiong, and B. Zuo, "Association of 3 polymorphisms in porcine troponin I genes (TNNI1 and TNNI2) with meat quality traits," J. Appl. Genet. 51(1):51-57 (2010).
H. Yang, Z. Xu, Z. Ma, Y. Xiong, C. Deng, and B. Zuo, "Molecular cloning and comparative characterization of the porcine troponin I family," Anim. Biotechnol. 21(1):64-76 (2010).
R. Zasadny and K. Kwiatek, "Validation study of a new procedure for measuring insoluble impurities in animal fat," J. Anim. Feed Sci. 15(2):337-44 (2006).
Y. T. Zhou, Z. W. Wang, M. Higa, C. B. Newgard, and R. H. Unger, "Reversing adipocyte differentiation: implications for treatment of obesity," Proc. Natl. Acad. Sci. USA 96(5):2391-95 (1999).
Chen, et al., "Porcine Troponin I: A Thermostable Species Marker Protein" Meat Science, vol. 61, No. 1, pp. 55-60, May 2002.
Fumiere, et al., "Methods of Detection, Species Identification and Quantification of Processed Animal Proteins in Feedingstuffs" Biotechnologie, Agronomie, Societe et Environment, vol. 13, pp. 59-70, 2009.
Chen et al., "Monoclonal Antibodies to Porcine Thermal-Stable Muscle Protein for Detection of Pork in Raw and Cooked Meats" Journal of Food Science, vol. 63, No. 2, pp. 201-205, 1998.
International Preliminary Report on Patentability Report dated Mar. 12, 2015 in corresponding International Application No. PCT/IB2013/056896.

(Continued)

*Primary Examiner* — Andrea S Grossman
(74) *Attorney, Agent, or Firm* — Fox Rothschild LLP

(57) ABSTRACT

A method for extracting protein from a fat sample is described comprising the steps of separating solidified fat and solid residues from a centrifuged mixture of protein, fat, other solid materials and aqueous solution of phosphate buffered saline to form an aqueous phase containing the protein. The aqueous phase is then filtered through a filter to separate a clear protein extract from the mixture.

28 Claims, 2 Drawing Sheets

(56) References Cited

OTHER PUBLICATIONS

International Preliminary Report on Patentability Report dated Mar. 12, 2015 in corresponding International Application No. PCT/IB2013/058019.

O. Abbas, J.A.F. Pierna, R. Codony, C. von Hoist, and V. Baeten, "Assessment of the discrimination of animal fat by FT-Raman spectroscopy," J. Mol. Struct. 924-26:294-300 (2009).

M. Ahmed, M.J. Neville, M.J. Edelmann, B.M. Kessler, and F. Karpe, "Proteomic analysis of human adipose tissue after rosiglitazone treatment shows coordinated changes to promote glucose uptake," Obesity (Silver Spring) 18(1):27-34 (2010).

A.A. Aida, Y.B.C. Man, C.M. Wong, A.R. Raha, and R. Son, "Analysis of raw meats and fats of pigs using polymerase chain reaction for Halal authentication," Meat Sci. 69(1):47-52 (2005).

A.A. Aida, Y.B.C. Man, A.A. Hassan, A.R. Raha, and R. Son, "Specific polymerase chain reaction (PCR) analysis of raw meats and fats of pigs for halal authentication," Middle East Journal of Scientific Research 7(6):1008-13 (2011).

A.A. Aida, Y.B.C. Man, A.R. Raha, and R. Son, "Detection of pig derivatives in food products for halal authentication by polymerase chain reaction-restriction fragment length polymorphism," J. Sci. Food Agr. 87(4):569-72 (2007).

S. Bellorini, S. Strathmann, V. Baeten, O. Fumiere, G. Berben, S. Tirendi, and C. von Hoist, "Discriminating animal fats and their origins: assessing the potentials of Fourier transform infrared spectroscopy, gas chromatography, immunoassay and polymerase chain reaction techniques," Anal. Bioanal. Chem. 382(4):1073-83 (2005).

E.G. Bligh and W.J. Dyer, "A rapid method of total lipid extraction and purification," Can. J. Biochem. Physiol. 37 (8):911-17 (1959).

S. Boulant, R. Montserret, R.G. Hope, M. Ratinier, P. Targett-Adams, J.P. Lavergne, F. Penin, and J. McLauchlan, "Structural determinants that target the hepatitis C virus core protein to lipid droplets," J. Biol. Chem. 281(31):22236-47 (2006).

C.L. Brennan, M. Hoenig, and D.C. Ferguson, "GLUT4 but not GLUT1 expression decreases early in the development of feline obesity," Domest. Anim. Endocrin. 26(4):291-301 (2004).

Y.B.C. Man, H.L. Gan, I. NorAini, S.A.H. Nazimah, and C.P. Tan, "Detection of lard adulteration in RBD palm olein using an electronic nose," Food Chem. 90(4):829-35 (2005).

Y.B.C. Man, and M.E.S. Mirghani, "Detection of lard mixed with body fats of chicken, lamb, and cow by Fourier transform infrared spectroscopy," Journal of the American Oil Chemists Society 78(7):753-761 (2001).

Y.B.C. Man, Z.A. Syahariza, and A. Rohman, "Discriminant analysis of selected edible fats and oils and those in biscuit formulation using FTIR spectroscopy," Food Anal. Methods 4(3):404-09 (2011).

F-C. Chen, Y-H. P. Hsieh, and R. C. Bridgman, "Monoclonal antibodies to porcine thermal-stable muscle protein for detection of pork in raw and cooked meats," J. Food Sci. 63: 201-05 (1998).

F-C. Chen, and Y-H. P. Hsieh, "Porcine troponin I: a thermostable species marker protein," Meat Sci. 61(1):55-60 (2002).

F-C. Chen Y-H. P. Hsieh, R. C. Bridgman, "Monoclonal antibody-based sandwich enzyme-linked immunosorbent assay for sensitive detection of prohibited ruminant proteins in feedstuffs," J. Food Prot. 67:544-49 (2004).

I. Chernukha, "Comparative study of meat composition from various animal species," International 56th Meat Industry Conference. Tara, Serbia: technologija mesa, 167-71 (2011).

S. T. Chin, Y. B. C. Man, C.P. Tan, and D.M. Hashim, "Rapid Profiling of Animal-Derived Fatty Acids Using Fast GC x GC Coupled to Time-of-Flight Mass Spectrometry," Journal of the American Oil Chemists Society 86(10):949-58 (2009).

B.B. De Taeye, C. Christophe Morisseau, J. Coyle, J.W. Covington, A. Luria, J. Yang, S.B. Murphy, D.B. Friedman, B.B. Hammock, and D.E. Vaughan, Expression and regulation of soluble epoxide hydrolase in adipose tissue, Obesity 18:489-498 (2010).

P. Dugo, T. Kumm, A. Fazio, G. Dugo, and L. Mondello, "Determination of beef tallow in lard through a multidimensional off-line non-aqueous reversed phase-argentation LC method coupled to mass spectrometry," J. Sep. Sci. 29(4):567-75 (2006).

ECSSC, Opinion on the safety of tallow derivatives from cattle tallow (1999).

B. Friguet, L. Djavadi-Ohaniance, J. Pages, A. Bussard, and M. Goldberg, "A convenient enzyme-linked immunosorbent assay for testing whether monoclonal antibodies recognize the same antigenic site. Application to hybridomas specific for the beta 2 subunit of *Escherichia coli* tryptophan synthase," J. Immunol. Methods 60:351-58 (1983).

G. Gondret, B. Guevel, E. Com, A. Vincent, and B. Lebret, "A comparison of subcutaneous adipose tissue proteomes in juvenile piglets with a contrasted adiposity underscored similarities with human obesity," J. Proteomics 75(3):949-61 (2012).

K. Hiramoto, K. Kido, and K. Kikugawa, "DNA Breaking by Maillard Products of Glucose Amino-Acid Mixtures Formed in an Aqueous System," J. Agr. Food Chem. 42(3):689-94 (1994).

Y-H. P. Hsieh, F-C. Chen, and N. Djurdjevic, "Monoclonal antibodies against heat-treated muscle proteins for species identification and end-point cooking temperature determination of cooked meats," Quality Attributes of Muscle Foods. Xiong, Ho and Shahidi (eds.). Kluwer Academic/Plenum Publishers, N.Y. 287-306 (1999).

G. Iacobellis, D. Corradi, and A.M. Sharma, "Epicardial adipose tissue: anatomic, biomolecular and clinical relationships with the heart," Nat. Clin. Pract. Cardiovasc. Med. 2(10):536-43(2005).

D. Indrasti, Y.B.C. Man, S. Mustafa, and D. M. Hashim, "Lard detection based on fatty acids profile using comprehensive gas chromatography hyphenated with time-of-flight mass spectrometry," Food Chem. 122(4):1273-77 (2010).

H-J. Jacobsen and R. Greiner, "Methods for detecting genetic manipulation in grain legumes," Jackson, J. F. & Linskens, H. F., editors. Molecular methods of plant analysis: Testing for genetic manipulation in plants New York: Springer, 64 (2002).

M. Kagawa, K. Matsubara, K. Kimura, H. Shiono, and Y. Fukui, "Species identification by the positional analysis of fatty acid composition in triacylglyceride of adipose and bone tissues," Forensic. Sci. Int. 79(3):215-26 (1996).

E.E. Kershaw, and J.S. Flier, "Adipose tissue as an endocrine organ," J. Clin. Endocrinol. Metab. 89, 2548-56 (2004).

H.A. Kuiper, "Summary report of the ILSI Europe workshop on detection methods for novel foods derived from genetically modified organisms," Food Control 10(6):339-49 (1999).

A. Lazarev, G. Smejkal, I. Romanovsky, A. Kwan, H. Cao, G.S. Hotamisligil, and A.R. Ivanov, "Proteomic analysis of murine adipose tissue using pressure cycling technology and high resolution tandem mass spectrometry," US HUPO 3rd Annual Conference, Seattle, WA (2007).

D. Lichtenberg, E. Opatowski and M.M. Kozlov, "Phase boundaries in mixtures of membrane-forming amphiphiles and micelle-forming amphiphiles," Biochim. Biophys. Acta 1508(12):1-19 (2000).

J.M.N. Marikkar, H. M. Ghazali, Y.B.C. Man and O.M. Lai, "The use of cooling and heating thermograms for monitoring of tallow, lard and chicken fat adulterations in canola oil," Food Research International 35 (10):1007-14 (2002).

J.M.N. Marikkar, H.M. Ghazali, Y.B.C. Man, T.S.G. Peiris and O. M.Lai, "Distinguishing lard from other animal fats in admixtures of some vegetable oils using liquid chromatographic data coupled with multivariate data analysis," Food Chem. 91(1):5-14 (2005).

M.S. Moawad, M.A. Tony and H.A. Aref, "Forensic identification of subcutaneous and perirenal adipose tissue samples in some in some farm animals using gas liquid chromatography," Mansoura. Vet. Med. J. XI(1): 13-20(2009).

N.H. Mohan, B. C. Sarmah, M. K. Tamuli, A. Das, and K. M. Bujarbaruah, "Electrophoretic profile of porcine adipose tissue and a method for extraction of soluble proteins from fat tissue," Indian J. Anim. Sci. 77(12):1248-50 (2007).

J.F. Montiel-Sosa, E. Ruiz-Pesini, J. Montoya, P. Roncales, M.J. Lopez-Perez, and A. Perez-Martos, "Direct and highly species-specific detection of pork meat and fat in meat products by PCR amplification of mitochondrial DNA," J. Agric Food Chem. 48(7):2829-32 (2000).

M. Motoyama, M. Ando M. K. Sasaki and H.O. Hamaguchi, "Differentiation of Animal Fats from Different Origins: Use of

(56) References Cited

OTHER PUBLICATIONS

Polymorphic Features Detected by Raman Spectroscopy," Appl. Spectrosc. 64(11):1244-50 (2010).

H.R. Mottram, Z.M. Crossman, and R.P. Evershed, "Regiospecific characterisation of the triacylglycerols in animal fats using high performance liquid chromatography atmospheric pressure chemical ionisation mass spectrometry," Analyst 126(7):1018-1024 (2001).

D.J. Murphy, "The biogenesis and functions of lipid bodies in animals, plants and microorganisms," Prog. Lipid Res. 40(5):325-438 (2001).

G. Rastogi, M.S. Dharne, S. Walujkar, A. Kwnar, M.S. Patole, and Y.S. Shouche, "Species identification and authentication of tissues of animal origin using mitochondrial and nuclear markers," Meat Sci. 76(4):666-74 (2007).

A. Rohman and Y.B.C. Man, "FTIR spectroscopy combined with chemometrics for analysis of lard in the mixtures with body fats of lamb, cow, and chicken," International Food Research Journal 17(3):519-26 (2010).

A. Rohman, Y. B.C. Man, P. Hashim and A. Ismail, "FTIR spectroscopy combined with chemometrics for analysis of lard adulteration in some vegetable oils," Journal of Food 9(2):96-101 (2011).

A. Rosenow, T.N. Arrey, F.G. Bouwman, J.P. Noben, M. Wabitsch, E.C.M. Mariman, M. Karas, and J. Renes, "Identification of Novel Human Adipocyte Secreted Proteins by Using SGBS Cells," J. Proteome Res. 9(10):5389-5401 (2010).

T. Sajic, G. Hopfgartner, I. Szanto, and E. Varesio, "Comparison of three detergent-free protein extraction protocols for white adipose tissue,"Anal. Biochem. 415(2):215-217.

A. Salgado-Somoza, E. Teijeira-Fernandez, A.L. Fernandez, J.R. Gonzalez-Juanatey, and S. Eiras, "Proteomic analysis of epicardial and subcutaneous adipose tissue reveals differences in proteins involved in oxidative stress," Am. J. Physiol. Heart Circ. Physiol. 299(1):H202-209 (2010).

M. Schreiner, R.G. Moreira and H.W. Hulan, "Positional distribution of fatty acids in egg yolk lipids," J. Food Lipids 13(1):36-56 (2006).

A. M. Seddon, P. Curnow and P. J. Booth, "Membrane proteins, lipids and detergents: not just a soap opera," Biochim. Biophys. Acta 1666(1-2): 105-117 (2004).

Sucipto, Irzaman, T.T. Irawadi, and A.M. Fauzi, "Potential of conductance measurement for lard detection," International Journal of Basic and Applied Sciences 11(5):26-30 (2011).

A. Szabó, H. Febel, L. Sugar, and R. Romvari, "Fatty acid regiodistribution analysis of divergent animal triacylglycerol samples—a possible approach for species differentiation," Journal of Food Lipids 14(1):62-77 (2007).

\* cited by examiner

SIMPLIFIED EXTRACTION METHODS FOR THE RAPID DETERMINATION OF SPECIES CONTENT OF ADIPOSE TISSUE BASED ON THE DETECTION OF TNI IN IMMUNOASSAYS

CROSS-REFERENCE TO RELATED APPLICATIONS

This application claims benefit of priority to U.S. patent application Ser. No. 14/421,626 filed Feb. 13, 2015, entitled "SIMPLIFIED EXTRACTION METHODS FOR THE RAPID DETERMINATION OF SPECIES CONTENT OF ADIPOSE TISSUE BASED ON THE DETECTION OF TNI IN IMMUNOASSAYS" of which the present application is a divisional application, which is a 371 national stage of International Patent Application No. PCT/IB2013/058019 filed Aug. 27, 2013, entitled "SIMPLIFIED EXTRACTION METHODS FOR THE RAPID DETERMINATION OF SPECIES CONTENT OF ADIPOSE TISSUE BASED ON THE DETECTION OF TNI IN IMMUNOASSAYS," which in turn claims priority to U.S. Provisional Patent Application No. 61/693,839 filed Aug. 28, 2012, entitled "SIMPLIFIED EXTRACTION METHODS FOR THE RAPID DETERMINATION OF SPECIES CONTENT OF ADIPOSE TISSUE BASED ON THE DETECTION OF TNI IN IMMUNOASSAYS." The entire contents and disclosures of these patent applications are incorporated herein by reference in their entirety.

This application also makes reference to U.S. patent application Ser. No. 14/421,289 filed Feb. 12, 2015, entitled "TROPONIN I (TN1) AS A SUITABLE MARKER PROTEIN FOR THE DETERMINATION OF ANIMAL SPECIES ORIGIN OF ADIPOSE TISSUE," which is a 371 national stage of International Patent Application No. PCT/IB2013/056896 filed Aug. 26, 2013, entitled "TROPONIN I (TN1) AS A SUITABLE MARKER PROTEIN FOR THE DETERMINATION OF ANIMAL SPECIES ORIGIN OF ADIPOSE TISSUE," which in turn claims priority to U.S. Provisional Patent Application No. 61/693,811 filed Aug. 28, 2012, entitled "TROPONIN I (TN1) AS A SUITABLE MARKER PROTEIN FOR THE DETERMINATION OF ANIMAL SPECIES ORIGIN OF ADIPOSE TISSUE." The entire contents and disclosures of these patent applications are incorporated herein by reference.

BACKGROUND

Field of the Invention

The present invention relates to a method of soluble protein extraction from adipose tissue.

Related Art

Existing methods of extracting proteins from adipose tissue are often not particularly easy or quick to perform.

SUMMARY

According to a first broad aspect, the present invention provides a method comprising the following steps: (a) separating solidified fat and other solid materials from a mixture to thereby form an aqueous phase containing soluble proteins, and (b) filtering the aqueous phase through a filter to thereby separate a protein extract from the mixture, wherein the mixture comprises an aqueous phase containing a phosphate buffered saline and containing the soluble proteins and insoluble and/or immiscible substances from a pre-warmed and ground fat sample.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE PREFERRED EMBODIMENTS

Definitions

Figure 1:
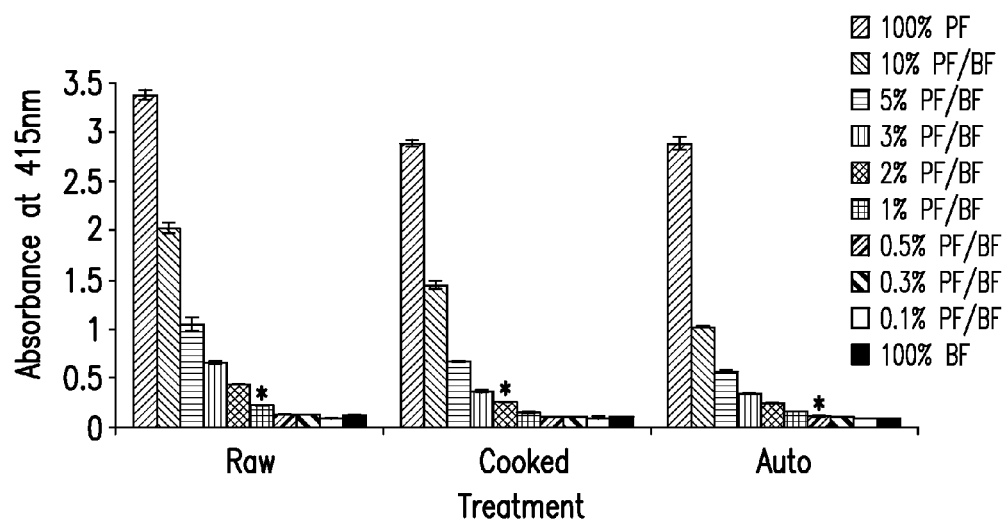
FIG. 1 shows bar graphs illustrating the detection limit of pork fat in raw, cooked and autoclaved beef fat using sandwich ELISA with purified MAb 8F10 as a capture antibody and biotin-conjugated MAb 5H9 as a detection antibody.

Where the definition of a term departs from the commonly used meaning of the term, applicant intends to utilize the definitions provided below, unless specifically indicated.

For purposes of the present invention, it should be noted that the singular forms, "a," "an" and "the" include reference to the plural unless the context as herein presented clearly indicates otherwise.

For purposes of the present invention, directional terms such as "top," "bottom," "upper," "lower," "above," "below," "left," "right," "horizontal," "vertical," "up," "down," etc., are merely used for convenience in describing the various embodiments of the present invention. The embodiments of the present invention may be oriented in various ways. For example, the diagrams, apparatuses, etc., shown in the drawing figures may be flipped over, rotated by 90° in any direction, reversed, etc.

For purposes of the present invention, a value or property is "based" on a particular value, property, the satisfaction of a condition, or other factor, if that value is derived by performing a mathematical calculation or logical decision using that value, property or other factor.

For purposes of the present invention, the term "computer" refers to any type of computer or other device that implements software including an individual computer such as a personal computer, laptop computer, tablet computer, mainframe computer, mini-computer, etc. The term "computer" also refers to electronic devices such as a scanner, a sensor, smartphone, an eBook reader, a cell phone, a television, a handheld electronic game console, a videogame console, a compressed audio or video player such as an MP3 player, a Blu-ray player, a DVD player, a microwave oven, etc. In addition, the term "computer" refers to any type of network of computers, such as a network of computers in a business, a computer bank, the Cloud, the Internet, etc. In one embodiment of the present invention, a computer may be employed to control the performance of one or more steps of the method of the present invention.

For purposes of the present invention, the term "contaminant fat" refers to undeclared fat of a particular species present in a sample mixture. Undeclared fat is the fat or its species origin that is not made known explicitly to the user on the food label, menu or by words.

For purposes of the present invention, the term "fat" refers to any type of solid or liquid fat that might contain protein residues.

For purposes of the present invention, the term "fat-containing" sample refers to a sample containing fat. A fat-containing sample may be made of only fat or may contain other materials such as a meat.

For purposes of the present invention, the term "reduced temperature" refers to a temperature less than the solidifying temperature of the fat.

For purposes of the present invention, the term "room temperature" refers to a temperature in the range of 20° C. to 25° C.

For purposes of the present invention, the term "to soften" refers to partially melting a solid fat-containing sample at an elevated temperature.

For purposes of the present invention, the term "species of TnI" refers to the TnI for a specific species.

For purposes of the present invention, the term "visual display device," the term "visual display apparatus" and the term "visual display" refer to any type of visual display device or apparatus such as a an LCD screen, touchscreen, a CRT monitor, LEDs, a projected display, a printer for printing out an image such as a picture and/or text, etc. A visual display device may be a part of another device such as a spectrometer, a computer monitor, a television, a projector, a cell phone, a smartphone, a laptop computer, a tablet computer, a handheld music and/or video player, a personal data assistant (PDA), a handheld game player, a head mounted display, a heads-up display (HUD), a global positioning system (GPS) receiver, etc. In one embodiment of the present invention, a visual display device may be employed to display to a user the results of one or more steps of the method of the present invention and/or the progress of one or more steps of the method present invention.

DESCRIPTION

A recent study reported that only DNA and a protein-based immunoassay could determine the species (ruminant) content of fat in meat and bone meals. DNA-based methods usually are not tissue-specific and are ineffective against samples that have undergone processes such as severe heat processing (e.g., canning) and hydrolysis, which damages DNA and hence reduces the yield and quality of the amount of DNA extracted from such processed foods samples. Besides, both fat-based and DNA-based methods have focused almost exclusively on the detection of animal fat in raw samples and hence cannot be guaranteed to be equally effective against heat-processed counterparts. Rapid and effective methods for the determination of fat species in a mixture have not been reported in the literature although such methods are urgently needed.

Immunoassays based on the specific antibody-antigen recognition have been widely accepted as a simple, rapid and specific analytical technique for agricultural and food analyses, either qualitatively or quantitatively. Usually the assay can be performed in a complicated sample mixture without laborious isolation or purification of the target analyte(s) from the sample. In order to develop an immunoassay for rapid species content determination, one critical element is the availability of species-specific antibodies as the probe to recognize the analyte (antigen). A species marker thus should firstly be identified in the adipose tissue which can be used as the target analyte for the antibody development. Most proteins are heat-labile and become insoluble after heating to certain degree. The conditions of an ideal species marker should be (1) that the antigen marker is present in the tissue in significant amount and is uniformly distributed throughout the tissue so that the detection result can be sensitive and representative, and (2) that the binding between the antibody and the antigen is stable after heat processing so that cooking would not affect the immunoreactivity for the detection.

In one embodiment, the present invention employs a universal and heat-stable muscle protein, troponin I (TnI), as a species marker protein in the adipose tissue. TnI is a ~23 KDa subunit protein of the myofibril protein "troponin." Although the presence of a number of proteins has been reported in animal fat tissue, the presence of TnI in the animal adipose tissue has now been discovered. Furthermore, TnI may be used for fat speciation. Because this protein has species-specific amino acid sequence regions, antibodies developed against this protein can be species specific if the binding site (epitope) is located at the species-specific region of the peptide. Such antibodies, including monoclonal or polyclonal antibodies, thus would be suitable to be used in an immunoassay to identify animal species not only in muscle but also in adipose tissues. While application of TnI as a species marker protein for the meat species identification has been reported in the literature, the use of Tn1 as a species marker for the species analysis of fat tissue has never been reported.

Immunoassays based on the detection and quantification of this marker protein are able to reliably, sensitively and rapidly detect animal species (pork, beef, poultry, etc.) in fat-in-fat or fat-in-meat mixtures at low levels (~1% w/w). Also, simplified protein extraction methods from the adipose tissue have also been developed. These simple methods only require aqueous extraction without homogenization of the sample admixture, although require a mild heat treatment. These methods will facilitate the analyses of variations of immunoassay in terms of time and costs. With the discovery of the fact that TnI can serve as a heat-stable species-marker in adipose tissue combined with the developed simple sample extraction methods, the application of TnI-based immunoassays for a rapid species identification and species content determination of animal fat in both raw and heat-processed samples can be accomplished. The success of this new application may be demonstrated by using several previously developed anti-TnI antibodies (porcine-specific, bovine-specific and all animal-specific) in several variations of immunoassays (ELISA, Western blot and lateral flow strip assay). There has never been any protein-based immunoassay reported in the literature for the rapid determination of species content of animal fat, especially it can be rapidly (minutes to few hours) done in either raw or cooked products with a low detection limit (approximately 1%).

Applications

Effective rapid methods for the species determination of fat tissue in a sample admixture are lacking but they are urgently needed. For example, hidden or fraudulent use of pork fat in a variety of food products to improve the texture, flavor or boost the bulk of the final product is an affront not only to Jews and Muslims who by the dictates of their religion are forbidden to consume anything derived from pig, it also violates the domestic and international food labeling laws. On the other hand, ruminant (cattle, deer, sheep and goat) proteins are banned in ruminant animal feed worldwide for the prevention of fatal prion diseases (mad cow disease and human Creutzfeldt-Jakob disease). Contamination of any ruminant tissue including adipose tissue would impose risks of transmitting prions from infected animals. Furthermore, in recent times there is a preference to use vegetable oil in place of animal fat in food processing because of the unhealthy fatty acid profile of animal fat. Among animal fats, pork and beef fats are most commonly used. Accordingly, the use of pork or beef fat, which traditionally had been the choice of fat for deep frying because they are cheap and stable, is restricted to only foods where its unique flavor is desirable. Unfortunately, adulteration of vegetable oils with animal fat in the formulation of shortenings, margarines and other specialty food oils is a common practice. Therefore, rapid methods for the sensitive detection of target materials in raw, cooked or rendered products are desired for consumer protection. Currently, immunoassay kits for the species identification of muscle tissue are available commercially (ELISA Technologies Inc., Neogen Co.) However, these assays were not designed and cannot detect the presence of target fat tissue in the sample according to the instructed sample preparation procedures which target muscle proteins.

A series of thermal-stable, species-specific antibodies may be used for the detection of a number of animal proteins such as tropomyosin, troponin, myosin, sarcoplasmic proteins, blood cellular and serum proteins in raw and cooked products. It has now been found that substantial amounts of proteins can be extracted from muscle-free adipose tissue even after cooking. Adipose tissue typically contains about 2% proteins, mainly collagen.

In animal fat products about 0.15% are insoluble impurities, about 85% of which is proteinaceous. Among these proteins, it is possible to identify the thermal-stable 23 KDa TnI to be the most suitable antigenic protein in adipose tissue for species-specific antibody development. Any immunoassays using species-specific anti-TnI antibodies can now be used not only for speciation in muscle samples but also in fat tissue and products, both raw and cooked. However, the new sample extraction methods should be employed to perform the appropriate immunoassay.

Fat Species Adulteration has been a Widespread Problem

Oils and fats have long played an important role as an essential nutrient in the human diet and are derived either from plant or animal sources. Adipose tissue of livestock animals is a major by-product obtained from meat processing and is often used as an ingredient in meat and food products (Aida et al. 2007 (Reference 5); Abbas et a. 2009 (Reference 1)). Among animal fats, pork and beef fats are most commonly used. Pork fat has been more widely used in meat and food industries to improve the texture, flavor and/or boost weight. However, food containing ingredients derived from a porcine source may cause serious concerns in the view of some religions, such as Islam and Judaism, and for vegetarians. Adulterating vegetable oils with tallow may present a health risk as the possibility of tallow carrying the infectious agent-prion that causes transmissible spongiform encephalopathy (TSE) has been reported (ECSSC 1999 (Reference 20)). Adulteration with less valuable or undeclared meat or fat species is prevalent worldwide and has been a serious concern among customers and food manufactures. Species adulteration in food or feed products may also cause other serious problems for safety and health reasons such as species-associated pathogen contaminations and allergic reactions in sensitized individuals (Hsieh et al., 1999 (Reference 24)). There are also those who refrain from consuming these edible animal fats for health reasons because of their unhealthy fatty acid profile which have been implicated in such diseases as cancers, hypercholesterolemia, multiple sclerosis and coronary heart disease.

Methods for Fat Species Identification and Fat Species Content Determination

The current global nature of the food trade with its intricate complexities has increased the potential for such fraudulent activities. The increased awareness among consumers regarding the ingredients used in the formulation of foods has made efforts by stakeholders (manufacturers, regulators, researchers and consumers) to authenticate the species origin of edible fats a priority.

There are also other reasons for which methods for fat speciation have been developed such as for authentication of fats used in feed formulation as a BSE control measure (Abbas et al. 2009 (Reference 1); Bellorini et al. 2005 (Reference 6)), for forensic purposes (Kagawa et al. 1996 (Reference 28); Moawad et al. 2009 (Reference 35)), and as an indirect approach for meat speciation (Chernukha 2011 (Reference 16)). However, determining the identity of edible animal fats in processed foods or composite blends is a difficult task as the adulterant has a composition similar to the original fat or oil. In the past years, many analytical methods have been replied in the literature for the identification of origin of the animal fat. They mainly include fat-based methods and DNA-based methods. Fat-based methods rely on subtle differences in the chemical (fatty acid composition and/or their positional distribution on the triacylglycerol (TAG) molecule) or physical (molecular structure and melting/crystallization temperatures) nature of different edible animal fats to identify their species origin while deoxyribonucleic acids (DNA)-based methods detects species-dependent differences at the gene level.

Fat-Based Methods for Species Identification

Using the fatty acid profile as a means for species identification of edible animal fat is a challenging task as the fatty acid composition is greatly influenced by the dietary fat intake. The situation is even compounded in recent times where the fatty acid composition of animal tissues can be modified; for example as in enrichment with omega-3 fatty acids (Wood et al. 2004 (Reference 54)). This notwithstanding, species-specific differences in the digestion process of dietary fats (Raclot T., Holm C. and Langin D. 2001. "Fatty acid specificity of hormone-sensitive lipase." Implication in the selective hydrolysis of triacylglycerols. *J. Lipid Res.* 42(12):2049-2057 (2001) and Sato K., Suzuki K. and Akiba Y. "Species differences in substrate specificity of lipoprotein lipase purified from chickens and rats." *Comp. Biochem. Physiol. A. Mol. Integr. Physiol.* 119(2):569-573 (1998)) and the different nutrient demands of divergent species (which is ultimately reflected in the composition of the deposited lipids) (Kagawa et al. 1996 (Reference 28); Schreiner et al. 2006 (Reference 47)), have been exploited for species identification of fat. Typically, the fat is removed by saponification, converted to methyl esters, and the fatty acid (FA) pattern is analyzed by various techniques such as gas chromatography (GC), high performance liquid chromatography (HPLC), Fourier transform infrared (FIT) spectroscopy and near infrared (NIR). These techniques are almost often combined with chemometric techniques as principal component analysis (PCA) or linear discriminant analysis (LDA) to allow for the recognition of patterns from the large data sets typically generated by the use of such instruments. These methods although useful are laborious and require long testing times, require an experienced analyst and involve the use of expensive instruments. In addition, most of these methods tend to be effective only when the target is present in copious amounts. Besides interpretation of data is not clear-cut as different researchers have used different interpretations of the results to mean the same thing. Thus, alternative methods that are fast and low in cost for species identification of animal fat are highly desirable.

DNA-Based Methods for Species Identification

More recently, DNA molecules have become target molecules for species identification in foods because of their high stability and also their presence in most biological tissues. Specific amplification of a fragment of DNA by means of polymerase chain reaction (PCR) with subsequent fragment size verification upon gel electrophoresis is the simplest DNA-based strategy for species identification of animal tissues. More species-specific variations such as restriction fragment length polymorphism (RFLP) PCR (Aida et al. 2005, 2007, 2011), analysis of single strand conformation polymorphism (SSCP) PCR, sequencing of fragments, and simultaneous amplification of two or more fragments with different primer pairs (multiplex PCR) have been developed for species identification of edible animal fats. With these DNA-based methods, mitochondrial DNA is generally the target as it has several advantages over nuclear DNA (Rastogi et al. 2007 (Reference 41)). These methods could be equally applied for species identification of meat and fat or other tissues because DNA is an universal biomarker in all biological tissues. Although DNA-based methods are useful and have been considered as a convincing method for speciation, the success of these DNA techniques is dependent on the amount and quality of DNA extracted from the sample. Several food processes have a negative influence on the accessibility and extraction of appropriate DNA material for PCR and hence renders DNA-based methods ineffective in certain instances. DNA is degraded by high temperature food processes either directly (Bellorini et al. 2005 (Reference 6)) or indirectly through the action of radicals furnished by Maillard products that are generated during the thermal processing (Hiramoto et al. 1994 (Reference 23)). DNA may also be degraded during such food processes as hydrolysis (both enzymatic and chemical) and mechanical treatment (shear forces) (Jacobsen and Greiner 2002 (Reference 27)). Typically, DNA is not detectable in highly heat-processed food products, hydrolyzed products, and highly purified products (e.g. refined oils) (Kuiper 1999 (Reference 30)). In addition, DNA-based methods also require the use of major instruments, are prone to contamination, require highly technical skills, and are not feasible for large sample screening or rapid field testing. Both fat-based and DNA-based techniques have been shown useful for species identification of animal fat. However, besides the shortcomings of these methods mentioned above, these methods have focused almost exclusively on speciation of raw fat. Thus, although the usefulness of these methods for identifying the species origin of raw fat samples can be vouched for, the same cannot be said in situations in which these animal fats are present in processed foods.

Protein-Based Methods for Species Identification

Protein-based immunoassays are based on the specific binding reaction between an antigen and the antibody. Immunoassays do not require major investment in equipment, are easy to perform, need only small quantities of test sample and immunoreagents, are amenable to field testing and have the capacity for large-scale screening. Immunoassays are therefore widely accepted by regulatory bodies as a quick and sensitive method for screening and monitoring substances in food and agricultural products. In addition, immunoassays can be performed in a complicated sample mixture without laborious isolation or purification of the target analyte(s) from the sample. If sufficient amount of soluble proteins can be extracted from the adipose tissue, the development of more convenient and rapid methods based on immunochemical principles for animal fat detection/speciation would be advantageous and desirable.

Requirements for Protein-Based Immunoassay Development

The performance of the immunoassay rests primarily on the nature, quality, and availability of the detecting antibodies to capture the target protein antigen (analyte) in a sample extract. In order to develop an immunoassay for species identification of adipose tissue, it is necessary that a suitable antigen (usually a protein) biomarker be selected for the purpose. Although proteins are generally more heat-labile than DNA and most current immunoassays target native proteins, some proteins are highly stable and can be used as the antigen for antibody development and antibody recognition. The conditions of an ideal species marker should be that the antigen marker is present in the tissue in significant amount and is uniformly distributed throughout the tissue so that the detection result can be sensitive and representative, and that the binding between the antibody and the antigen is stable after heat processing so that cooking would not affect the immunoreactivity for the detection.

Identified Proteins in Adipose Tissue

Adipose tissue or fat tissue is a kind of loose connective tissue composed of mature adipocytes, fibroblasts, immune cells, adipose tissue matrix and blood vessels. Approximately 60 to 85% of the weight of adipose tissue is lipid with 90 to 99% of the lipid being triglyceride. The remaining weight of adipose tissue is composed of water (5 to 30%) and protein (2 to 3%) (Schaffler A., Schölmerich J. and Büchler C. "Mechanisms of Disease: adipocytokines and visceral adipose tissue-emerging role in intestinal and mesenteric diseases." *Nat. Clin. Pract. Gastroenterol. Hepatol.* 2, 103-111 (2005)). Adipose tissue secretes different types of proteins that play important roles in homeostasis and metabolism through their autocrine, paracrine, and endocrine effects. The term adipokine has been suggested to describe all proteins secreted from any type of adipocyte (Trayhurn et al. 2011 (Reference 51)). Over the past century, proteins secreted from adipose tissue have been investigated. Physiologists have reported that a number of proteins, such as cytokines and cytokine-related proteins, chemokines, other immune-related proteins, proteins involved in the fibrinolytic system, complement and complement-related proteins for lipid metabolism or transport, and enzymes involved in steroid metabolism are secreted in adipose tissue (Kershaw and Flier 2004 (Reference 29); Rosenow et al. 2010 (Reference 44)). In addition, adipose tissue has also been shown to secrete contractile muscle proteins. For instance, muscle proteins including myosin, tropomyosin-2, tropomyosin α-3, and tropomyosin α-4 have been detected in human and porcine adipose tissues (Rosenow et al. 2010 (Reference 44); Ahmed et al. 2010 Reference 2)).

Troponin I as a Suitable Marker Protein for the Determination of Animal Species Origin of Adipose Tissue It has been discovered that Troponin I (TnI) can be found in muscle-free adipose tissue in sufficient amount to allow TnI to be used a suitable species-marker protein for the species identification and species content determination of animal adipose tissue. TnI is a part of the muscle contractile protein, troponin which consists of three subunits, Troponin C (TnC), Troponin T (TnT) and Troponin I (TnI). TnI, the inhibitory subunit of the Troponin complex, consists of a family of three muscle-specific myofibrillar proteins involved in the calcium-sensitive regulation of contraction in both skeletal and cardiac muscle (Wilkinson and Grand 1978 (Reference 53). TnI-skeletal-slow-twitch (TnI1), Tn1-skeletal-fast-twitch (TnI2) and TnI-cardiac (Tn3) which are the individual members of this family, are encoded by separate genes in mammals and expressed differentially in various classes of muscle fibers (Yang et al. 2010 (Reference 55)). As TnI has been classified as muscle protein in the past years, the presence of TnI in adipose tissue has never been reported, however, the concept was indirectly supported by Yang et al. 2010 (Reference 56) who reported from their gene expression profiling studies that the TnI1 and TnI2 genes also to be expressed in many other tissues studied including porcine adipose tissue.

In one embodiment, the present invention provides a simple and rapid method for protein extraction and sample preparation from the muscle-free adipose tissue. These methods enable a rapid extraction of substantial amount of soluble proteins including troponin I from the adipose tissue in a fat mixture of fat-meat mixture. This feature not only increases the detection sensitivity of an immunoassay but also facilitates protein studies for various biochemical, biological, and physiological purposes.

Slightly modified sample preparation procedure was also developed for the optimized condition in a user-friendly field test immunoassay variation, lateral flow immunochromatographic strip test. These sample preparation procedures enable the immunoassays to detect very low levels of fat in raw, cooked or autoclaved sample mixtures.

Current methodologies for species identification are mainly fat-based methods and DNA-based methods. However, protein-based methods such as immunoassays that rely on the detection of protein components or residual insoluble impurities in animal fat seem to have a more promising potential as they can overcome the shortcomings of DNA-based and fat-based methods. Various methods have been devised for fat sample preparation prior to analysis using fat-based, protein-based, or DNA-based methods of fat speciation. These sample preparation methods entail the extraction of DNA-material (DNA-based methods), protein material (protein-based methods), and lipid components (fat-based methods). Although these methods vary individually in terms of reagents and instrumentation, typically they are based on the same principles. Following are some of these methods that have been devised for fat sample preparation with emphasis on extracting proteins from fat samples for analysis using protein-based methods.

Fat Sample Preparation for DNA-Based Methods

Most of the DNA-based methods (Aida et al. 2005, 2007, 2011 (Reference 3, Reference 4 and Reference 5) developed for speciation of edible animal fat relied on protocols prescribed with a commercial DNA kit to extract DNA from fat samples. There are several DNA extraction kits that are available commercially and can also be utilized for DNA extraction from animal fat. These kits are based on the same principles which involve destruction of cell structures and consequent release of nucleic acids from the nucleus (cell lysis), DNA separation from proteins and lipids, and DNA purification from PCR inhibitors. Thus, these DNA extraction kits differ in terms of the chemicals that are utilized at each phase. Several organic solvents such as chloroform, phenol, isoamyl alcohol either singly or in combination with one another are used in the DNA separation step to form complexes with proteins and lipids causing them to precipitate out of solution. Ethanol or isopropanol are used to precipitate DNA in the final DNA purification step. The advantage of using these DNA kits is to increase yield without compromising speed. Some of these kits when automated allow DNA to be purified in as little as 15 minutes. These kits, however, are not inexpensive. For some of the DNA-based methods that have been developed for animal fat speciation, DNA extraction had to be performed manually (Montiel-Sosa et al. 2000 (Reference 37)) which is time consuming and laborious. Irrespective of whether DNA is extracted with the aid of a kit or manually, both approaches involve the use of dangerous organic solvents such as chloroform and isoamyl alcohol, and require a fair level of expertise.

Fat Sample Preparation for Fat-Based Methods

In the case of fat-based methods, sample preparation may be as simple as using the fat sample as-is or just melting the fat sample, or could be laborious, involving several steps, depending on the objective (measuring a physical characteristic or chemical characteristic) and choice of instrumentation and the nature of the sample. Fat-based methods that are available currently for species identification of edible animal fat rely on physical differences (e.g. melting and crystallization characteristics) or chemical differences (e.g. fatty acid profile) to determine the species origin of edible animal fat. Those methods that rely on the measurement of physical differences using various sophisticated instruments require little to no sample preparation prior to analysis. For example, in the study by Motoyama et al. (2010) (Reference 38) where Raman spectroscopy was utilized to examine polymorphic differences between pork and beef fats as a means of distinguishing between these two types of fats, the fat sample preparation involved simply melting the fat at 50° C. In the case of the study by Marikkar et al. (2002) (Reference 33) where differences in the melting and crystallization (measured using differential scanning calorimetry, DSC) characteristics were employed to detect the presence of pork fat and beef fat as adulterants in canola oil, fat samples were used as-is. Other fat-based methods based on the measurement of physical differences (Che Man et al. 2005 (Reference 1); Che Man and Mirghani 2001 (Reference 11); Rohman and Che Man 2010 (Reference 42); Rohman et al. 2011 (Reference 43); Sucipto et al. 2011 (Reference 49) to identify the species origin similarly require little or no sample preparation. Although it appears that such fat-based methods have an advantage in terms of ease of sample preparation, it is only because these methods involved the use of pure fat as samples. In the case in which the fat sample (as lard or tallow) is present in a matrix, the fat would have to be extracted using common fat extraction methods that are time-consuming, laborious, and involve the use of hazardous organic solvents. For example, the use of FTIR (Fourier Transform Infrared Spectroscopy) to measure the presence of lard in pork fat (Che Man et al. 2011 (Reference 12)) involved the extraction of fat from the biscuits using the Soxhlet method by AOAC, a lengthy process that requires a day for a single analysis. As a matter of fact, because of the cumbersome nature of the Soxhlet process, it is not favored for routine analysis and is used typically as a standard reference method.

On the other hand, fat-based methods (Chin et al. 2009 (Reference 17); Dugo et al. 2006 (Reference 19); Indrasti et al. 2010 (Reference 26); Marikkar et al. 2005 (Reference 34); Mottram et al. 2001 (Reference 39); Szabo et al. 2007

(Reference 50); Vaclavik et al. 2011 (Reference 52)) for fat speciation that rely on chemical differences in triacylglycerol (TAG) molecule or fatty acid profiles involve time-consuming sample preparation procedures. Typically for those methods based on the analysis of TAG profile, fat is first extracted from the fat tissue and then TAG purified from other contaminants (e.g. phospholipids, sterols and fat-soluble vitamins) using chromatographic techniques. For those methods that rely on differences in the fatty acid profile, the purified TAG molecule is then hydrolyzed either enzymatically or chemically and the released fatty acids are converted into fatty acid methyl esters using methanol prior to analysis. Besides the fact that these sample preparation procedures are lengthy, they also involve the use of hazardous chemicals. As was the case was with fat-based methods that rely on physical differences, the sample treatments mentioned in this paragraph have similarly been performed on pure fat samples or mixtures (fat-in-fat and fat-in-vegetable oil samples) thereof. Thus, in situations that require the presence of, say, lard or tallow in a heterogeneous matrix (e.g. pork fat in meat) to be detected, the sample preparation procedure may have to include a further processing step to eliminate non-lipid components.

Fat Sample Preparation for Protein-Based Methods

As already mentioned, protein-based methods such as immunoassay offer several advantages over fat-based and DNA-based methods for edible animal fat speciation. However, compared to other tissues, adipose tissue contains a relatively smaller percentage of protein by weight. Thus, the success of these protein-based methods, among others, will depend on the extraction of as much protein as possible from the fat sample. Several methods to extract protein from adipose tissue have been reported in the literature in an effort to address obesity and obesity-related diseases (Salgado-Somoza et al. 2010 (Reference 46)). Studies on the role of adipokines in livestock fat deposition, to help provide meat varieties that are leaner and healthier, have also motivated the development of methods to extract proteins from adipose tissue. Monitoring the protein content of inedible animal fat that are used in feed formulations have become important in enforcing labeling laws promulgated to control the spread of BSE. Accordingly, methods to extract protein (as insoluble impurities) from animal fat meant for livestock have also been reported in the literature. The following few sections will look at these extraction protocols with an emphasis on their applicability for immunoassays.

Adipose Tissue Protein Extraction Methods for Obesity and Obesity-Related Disease Research Salgado-Somoza et al. (2010) (Reference 46) studied the protein expression profiles of adipose tissue with special attention to proteins related to oxidative stress. Their extraction protocol first involved rinsing of a weighed sample in physiological salt solution (PSS) then centrifuging at 300 g to remove residual blood. Then lysis buffer was added and the mixture ground with a sample grinding kit. Proteins were then precipitated with a commercial 2-D Clean-Up kit in accordance with the manufacturer's instructions. Precipitated proteins were then re-suspended in sample solution consisting of 7M urea, 2M thiourea, 4% CHAPS, and 40 mM dithiothreitol (DTT). Because this protein extraction method is being used for an immunoassay, the chemicals used in the extraction are not only potentially toxic (as stated by the manufacturer) but are well known protein denaturants (sodium dodecyl sulfate (SDS), urea), which may destroy epitopes, particularly conformational epitopes, and hence may not be an appropriate sample preparation protocol for immunoassay. The use of DTT, which is a strong reducing agent, may also prevent antibody-protein binding in immunoassays in situations in which the epitope recognized by the antibody happens to contain disulfide bonds.

Several other studies also developed protein extraction methods for murine adipose tissue to enable future proteomic investigations of murine disease models (Lazarev et al. 2007 (Reference 31), De Taeye et al. 2010 (Reference 18), Sajic et al. 2011 (Reference 45)). These methods all involved lengthy procedures including homogenization, buffer extraction, centrifugation, protein concentration and precipitation, reduction, alkylation, etc. Some steps such as reduction and alkylation can be omitted for the purposes of preparing the sample for immunoassay to reduce the sample preparation time. However, the use of the protein denaturant (urea), organic solvents (methanol, chloroform) or detergent (Triton X) in the buffer, may render this method unsuitable for immunoassay applications. Application of detergents frequently leads to protein entrapment in the micelles resulting in protein loss and consequently poor protein yield (Seddon et al. 2004 (Reference 48). Given that the protein content of adipose tissue is a small part of the total tissue mass, protocols that ensure maximum recovery proteins are more desirable.

The adipose tissue protein extraction method by Zhou et al. (1999) (Reference 58) in their obesity research, is the most suitable as a sample preparation protocol for immunoassays. In their protocol, protein was extracted from rat epididymal fat by first washing the fat sample in ice-cold phosphate-buffered saline (PBS) followed by homogenization in a buffer (pH 7.5) containing 20 mM Tris-Ha, 1 mM ethylenediaminetetraacetic acid (EDTA), and 0.1 mM phenylmethane sulfonyl fluoride. The extract was then centrifuged at 8000 g for 5 minutes and again at 100,000 g for 1 hour at 4° C. and the infranatant contain the protein isolated. This method has the advantage of being fast, easy to perform, and involves the use of chemicals that are gentle on proteins. However, in immunoassays in which the binding of the antibody to its antigenic protein is metal-dependent, the use of the chelator EDTA in the buffer may still render this protocol unsuitable.

Adipose Tissue Protein Extraction Methods for Livestock Fat Deposition Research.

Mohan et al. (2007) (Reference 36) reported on the development of a technique for extracting soluble proteins from porcine adipose tissue to facilitate research on fat deposition in livestock. Two grams (2 g) of fat tissues pre-washed with normal saline are crashed in the frozen state in a mortar with pestle in the presence of 10 mL homogenization buffer [1% SDS, 3M sucrose, 25 mM HEPES, and protease inhibitors (2 mM EDTA and 1 mM phenyl sulfonyl fluoride) at 4° C. About 0.5 to 1 g of purified sea sand is also added to the mix to enhance the grinding action. The homogenate is allowed to stand for 1 hour, filtered, and then centrifuged at 1000 g for 30 minutes at 4° C. The proteins are then precipitated from the infranatant using trichloracetic acid (TCA). The precipitate is collected, washed twice in cold acetone, allowed to dry in air, and then dissolved in a small volume of 1% SDS prior to analysis. For the purposes of using this procedure as a sample preparation protocol for immunoassay, the extract can be used after the centrifugal stage without the need for the protein precipitation and further isolation steps to shorten the sample preparation time. However, the use of SDS in the homogenization buffer may unfold the proteins thereby rendering the technique unsuitable for immunoassays. The use of EDTA also may not be suitable for certain immunoassays as explained above. Mohan et al. (2007) (Reference 36) reported their extraction protocol to be a modification of an earlier protocol by Brennan et al. (2004) (Reference 9) which they (Mohan et al. 2007 (Reference 36)) mentioned in their report as being cumbersome. In the case of the study by Brennan et al. (2004) (Reference 9), homogenization of fat samples was done with a different buffer comprising of 1% Triton, 500 mM Tris-HCl and a complete protease inhibitor cocktail. Also, the protein precipitating buffer contained DTT in addition to the acetone and TCA that was used in the study by Mohan et al. (2007) (Reference 36). The protocol by Brennan et al. (2004) (Reference 9) also contained the post-protein purification steps of sonication in 1% Triton, 5 M urea and 62.5 mM Tris-base and centrifugation to solubilize the air-dried protein. Although these extra steps may be omitted to shorten the sample preparation time, the protocol is plagued by the use detergents and reducing agents that renders it unsuitable for immunoassays.

Gondret et al. (2012) (Reference 22) identified proteins and pathways associated with differences in body adiposity levels between French Basque pigs (which have a high potential for deposition of subcutaneous fat) and the Large White modern lean-type pig breed. Soluble proteins were extracted from adipose tissue of each type of pig by first homogenizing frozen adipose tissue samples with sucrose supplemented with EDTA and DDT. The mixture was then centrifuged and the soluble fraction which contains proteinaceous material collected below the fat cake. The soluble protein extract was further concentrated with centrifugal filter device prior to analysis. This extraction protocol has the advantage of being relatively fast and easy to perform. The use of DTT and EDTA, however, and as explained above, may render this protocol unsuitable for preparing soluble proteins extracts to be analyzed by immunoassay.

Adipose Tissue Protein Extraction Methods for BSE Surveillance

Regulation requires a minimum allowable insoluble impurities content of 0.15% in ruminant fat as a bovine spongiform encephalopathy (BSE) prevention strategy. This is because the insoluble impurities contain the protein material present in the original fat tissue. As such, fat samples containing <0.15% of insoluble impurities are essentially considered protein-free fat and hence technically considered to be devoid of the prion proteins responsible for BSE. To enforce such labeling regulations, Zasadny and Kwiatek (2006) (Reference 57) validated a new, less time-consuming method for determining the insoluble impurities content of fat derived from both ruminant and non-ruminant animals. Fat samples were heated to about 80° C. with constant stirring on a magnetic hot plate. One hundred gram (100 g) of the homogenized sample are then centrifuged at 3400×g for 10 minutes at 40° C., and the supernatant removed without disturbing the infranatant (insoluble impurities) which settled at the bottom of the tube. The insoluble impurities were rinsed briefly with 10 mL petroleum ether after which 85 mL of petroleum ether was added and the mixture centrifuged again at 3400 g at 20° C. This process is then repeated twice more and the defatted insoluble impurities filtered through glass microfiber filters. Finally, the extract is dried for 45 minutes at about 105° C. and cooled in a desiccator. This method shows that the results of naturally contaminated samples exhibited a high spread and expanded uncertainty of 0.11%. Note: petroleum ether is a hazardous chemical and, as such, the extraction protocol is performed under a chemical hood to avoid exposure.

In a related study to curb the spread of BSE, Bellorini et al. (2005) (Reference 6) compared four different techniques of differentiating between ruminant fat (tallow) and non-ruminant fat (lard). Among the techniques was a protein-based technique using a dipstick test kit (Agri-Screen, Neogen Corporation, MI, USA) previously developed for detecting ruminant meat bone meal (MBM) in feed. This technique involves extracting protein from tallow as follows. About 30 g of the fat sample was placed in an oven at 65° C. until molten and then centrifuged for 10 minutes at 40° C. at 3,500 rpm. The upper fat layer was then removed after which hexane was added and the mixture centrifuged again for 10 minutes at 30° C. This centrifugation was repeated a third time and after each centrifugation step the fat/hexane fraction was removed without disturbing the lower fraction containing the protein. After the third centrifugation step, 5 mL of extraction solvent (provided with the kit) along with a small portion of extraction additive (provided with the kit) at about ten times the weight of the residue was added prior to analysis with the dipstick. This method also uses hazardous organic solvents which seemed necessary for fat dissolution and elimination.

Need for Immunoassay-Friendly Methods to Extract Proteins from Adipose Tissue

From the submissions made above, methods for protein extraction from adipose tissue are rife in the literature for purposes of research on obesity and obesity-related diseases, research on fat deposition in livestock, and to enforce anti-BSE labeling laws. Although these methods are useful, they have certain limitations that make them unsuitable for application as a protein extraction protocols for immunoassays. These limitations include the use of dangerous organic solvents, the use of chemicals (denaturants, chelators and reducing agents) that may affect the epitopes, and/or the use of detergents which may affect protein recovery and also tend not to be compatible with subsequent protein analytical techniques. In addition, some of these methods tend to be laborious and time consuming, or involve the use of specialized clean-up kits that add to the cost. Accordingly, we have devised a simple, fast, and easy to perform protocol for extracting proteins from fat tissue that is devoid of the use of organic solvents, detergents, and chemicals that may destroy epitopes, such as a sample preparation protocol for performing an immunoassay to monitor the presence of fat content of a target species in food products.

Simplified Methods for the Extraction of Proteins from Adipose Tissue in Immunoassays Many methods have been devised to extract proteins from adipose tissue to address various research questions. However, these methods have limitations that make them unsuitable for use as a sample preparation protocol for immunoassays. After testing numerous extraction buffers and optimization trials in our laboratory, a very simple, fast, and easy protocol for extracting proteins from adipose tissue for use with immunoassays has been developed without compromising the protein quantity in the extract. These protocols require neither the use of organic solvent or other hazardous chemicals, nor the homogenization of the tissue. The general procedure for protein extraction from muscle-free ground fat tissue includes the following simple steps:

1. Pre-warm the ground fat sample in an oven for 30 to 60 minutes at 65° C. to soften the tissue.

2. Extract protein from a weighted portion of softened ground fat sample with 10 mM phosphate buffered saline (PBS) (174 g NaCl, 21.8 g $Na_2HPO_4$, 6.4 g $NaH_2PO_4$ dissolved in 2 L of distilled deionized water, pH 7.2)

3. Mix and shake the mixture vigorously at room temperature, then let the mixture sit for 2 hours.

4. Centrifuge the mixture at 3220 g for 30 min at reduced temperature 4° C. Then skim off the upper fat layer portion of the mixture. Next filter the lower aqueous phase (containing the protein) through a filter paper to produce a clear filtrate (protein extract) that is kept for analysis.

In one embodiment of the present invention, the antibodies used to detect TnI may be present on a sensor (biosensor or immunosensor) and the signal can be detected electronically or in many other ways such as by an optical fiber, etc.

In one embodiment, the present invention may employ variations of immunoassay (enzyme immunoassay, fluorescent immunoassay, radioisotope immunoassay, chemiluminescent immunoassay, immunosensors, etc.) automation. The automation of immunoassays has been popular in laboratories for high throughput screening routing tests. An advantage of immunoassay automation is that every procedure of various immunoassays can be operated by the automated instrument, not manually once the sample extracts have been prepared. The lateral flow strip test (an immunochromatographic method) can be read visually or by using a digitized device, such as a handheld type for field use, to obtain semi-quantitative readings.

In one embodiment, the ground fat sample may be pre-warmed for 30 to 120 minutes depending on the sample size at an oven heating temperature (the heat to which the sample is exposed) of 60 to 80° C.

In one embodiment of the present invention the mixture may sit for at least 1 hour before centrifuging the mixture.

In one embodiment, the mixture may be centrifuged at a reduced temperature in the range of 1° C. to 10° C. In one embodiment, the mixture is centrifuged for 15 to 60 minutes at speed sufficient to separate solidified fat and other solid residues from a liquid component of the mixture, wherein the liquid component contains the soluble proteins.

In various embodiments of the present invention, the solidified fat layer may be skimmed from the aqueous phase by methods such as using an appropriate size of spatula, spoon, rod, etc.

Suitable filters for use in various embodiments of the present invention to separate the clear filtrate from the aqueous phase of the centrifuged mixture include filters such as Whatman filter papers.

EXAMPLES

Example 1

Detection of pork fat in fat or meat mixtures with the sandwich ELISA using pork specific anti-TnI MAbs 5H9 and 8F10.
Methodology
Sample Preparation All visible muscle or blood is trimmed from the white adipose tissue. The surface of the sample is then rinsed by clean pure water. The sample is then patted dry and then ground twice using a household meat grinder. Lean meat samples are ground the same way as the fat samples.
Extracting Pork Fat Proteins from Pork Fat Fortified in Beef Fat (or Chicken Fat) Mixture For raw pork fat in beef fat (or chicken fat), a 10% (w/w) pork fat in beef fat (or chicken fat) is prepared by mixing 4.5 g of ground beef fat (or chicken fat) with 0.5 g of ground pork fat. The mixture is pre-heated in an oven for 30 minutes at 65° C. Ten percent (w/w) cooked pork fat in beef fat (or chicken fat) and autoclaved pork fat in beef fat (or chicken fat) are similarly prepared by mixing 4.5 g of beef fat (or chicken fat) with 0.5 g pork fat and then cooking (100° C. for 15 minutes) and autoclaving (121° C. for 15 min) the mixture, respectively. To the pre-warmed raw, cooked or autoclaved fat mixture, still hot with the fat melted, 10 mL (1:2 w/v) of extraction buffer is added, 10 mM PBS and stirred. The mixture is then transferred into a centrifuge tube. The tube is then shaken vigorously by hand and then transferred to a shaker and shaken in a horizontal position at 80 rpm for 1 hour. The mixture is then centrifuged at 3220 g for 30 min at 4° C. after which the solidified upper fat portion was skimmed off and the lower aqueous phase (containing the protein) filtered through Whatman Grade No. 4 filter paper and the filtrate (protein extract) is kept for analysis. Lower levels of adulteration of pork fat in beef fat (or chicken fat) are obtained by diluting 10% (w/w) samples with the appropriate amount of 100% non-porcine fat extract.

Extracting Pork Fat Proteins from Pork Fat Fortified in Beef Meat (or Chicken Meat Mixture)

For raw pork fat in beef meat (or chicken meat), a 10% (w/w) pork fat in beef meat (or chicken meat) sample is prepared by mixing 4.5 g of ground beef meat (or chicken meat) with 0.5 g of ground pork fat, and the mixture is pre-heated in an oven for 30 minutes at 65° C. Ten percent (w/w) cooked pork fat in beef meat (or chicken meat) and autoclaved pork fat in beef meat (or chicken meat) are similarly prepared by mixing 4.5 g of beef meat (or chicken meat) with 0.5 g pork fat. The mixture is then cooked (100° C. for 15 minutes) and autoclaved (120° C. for 15 minutes), respectively. To the pre-warmed, cooked or autoclaved fat in meat mixture, still hot with the fat melted, was added 25 mL (1:5 w/v) of extraction buffer (10 mM PBS), is added. The mixture is stirred and then transferred into a centrifuge tube. The tube is then shaken vigorously by hand and then transferred to a shaker and shaken in a horizontal position at 80 rpm for 1 hour. The mixture is then centrifuged at 3220 g for 30 minutes at 4° C. after which the solidified upper fat portion is skimmed off and the lower aqueous phase (containing the protein) filtered through Whatman Grade No. 4 filter paper and the filtrate (protein extract) is kept for analysis. Lower levels of adulteration of pork fat in beef meat (or chicken meat) are obtained by diluting 10% (w/w) samples with the appropriate amount of 100% non-porcine meat extract.
Sandwich ELISA Procedure One hundred microliter of the capture antibody, 8F10 purified IgG, diluted 1 to 750 in 10 mM phosphate buffered saline PBS (pH 7.2) to contain 0.13 µg protein per 100 µL per well was coated on the wells of a microplate and incubated at 37° C. for 2 hours. The plate was then washed three times with PBST (PBS containing 0.05% Tween 20 [v/v]) and then incubated for overnight at 37° C. with 200 µL of blocking buffer [1% bovine serum albumin (BSA) in PBS]. After washing the plate twice with PBST, 100 µL sample extract was added to the plate alongside controls. One hundred microliter (100 µL) of the detection antibody (biotin-conjugated 5H9) diluted 1:1275 to containing 0.08 µg protein was added to the plate and the plate incubated for 2 hours at 37° C. The plate was then washed three times with PBST and incubated with 100 µL of the enzyme substrate (streptavidin peroxidase polymer) for 2 hours at 37° C. At the end of the incubation period, 100 µL of color substrate (ABTS) was added to the plate and color was developed for 30 min at 37° C. The enzyme reaction was stopped by the addition of 100 µL of 0.2 M citric acid and the absorbance read at 415 nm.
Results By using the simple aqueous extraction method with PBS, substantial amounts of total soluble proteins can be rapidly extracted from raw, cooked and autoclaved fat and meat tissues from three animal species (pig, cattle, and poultry) (Table 1). In general, most soluble proteins are released from raw samples, followed by autoclaved and cooked fat and meat samples.

Table 1 shows the protein concentrations extracted with 10 mM PBS from raw, cooked and autoclaved adipose and lean muscle tissues. PF=pork fat; BF=beef fat; CF=chicken fat; BM=beef meat and CM=chicken meat.

TABLE 1

| Sample | Extracted protein concentration (mg/mL) |
| --- | --- |
| PF raw | 0.87 |
| PF cooked | 0.18 |
| PF autoclaved | 0.54 |
| BF raw | 0.87 |
| BF cooked | 0.17 |
| BF autoclaved | 0.78 |
| CF raw | 0.55 |
| CF cooked | 0.21 |
| CF autoclaved | 0.65 |
| BM raw | 1.97 |
| BM cooked | 0.77 |
| BM autoclaved | 3.06 |
| CM raw | 2.78 |
| CM cooked | 2.35 |
| CM autoclaved | 6.05 |

Previous studies in our laboratory have shown skeletal TnI (sTnI) to be a suitable thermostable marker protein for species identification in severely heated meats (Chen and Hsieh 2002 (Reference 14)). A sandwich ELISA (sELISA) for the detection of porcine skeletal muscle in meat and feed products has been reported (Liu and others 2006). The assay was based on MAb 8F10 and MAb 5H9 which recognizes mammalian skeletal TnI and porcine skeletal TnI, respectively. MAb 8F10 was used as the capture antibody and biotinylated MAb 5H9 as the capture antibody. Thus conceptually, this assay can also be appropriated to discriminate both raw and heat-treated pork fat from fat of other species due to the presence of sTnI in animal fat as an inherently expressed protein. When this sandwich ELISA is applied to the detection of pork fat in other fat (beef and chicken fats) mixtures and pork fat in other meat (beef and chicken meat) mixtures, low detection levels can be achieved, as demonstrated below in FIGS. 1, 2, 3 and 4.

FIG. 1 shows the detection limit of porcine fat in raw, cooked and autoclaved beef fat using sandwich ELISA with purified MAb 8F10 as the capture antibody and biotin-conjugated MAb 5H9 as the detection antibody. Soluble proteins were extracted from pork fat in raw, cooked and autoclaved beef fat mixtures using 25 mL and 10 mL of PBS for raw and heat-treated samples, respectively. PF=pork fat; PF/BF=pork fat in beef fat; and BF=beef fat. Results are expressed as A415±SD; n=3. * indicates detection limit.

Figure 2:
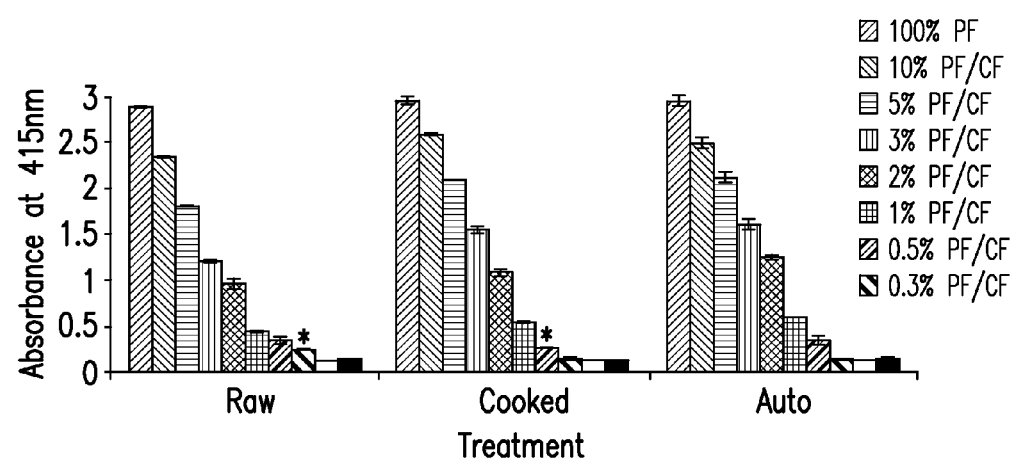
FIG. 2 shows bar graphs illustrating the detection limit of pork fat in raw, cooked and autoclaved chicken fat using sandwich ELISA with purified MAb 8F10 as a capture antibody and biotin-conjugated MAb 5H9 as a detection antibody.

FIG. 2 shows the detection limit of pork fat in raw, cooked and autoclaved chicken fat using sandwich ELISA with purified MAb 8F10 as the capture antibody and biotin-conjugated MAb 5H9 as the detection antibody. Soluble proteins were extracted from pork fat in raw, cooked and autoclaved chicken fat mixtures using 25 mL and 10 mL of PBS for raw and heat-treated samples, respectively. PF=pork fat; PF/CF=pork fat in chicken fat; and CF=chicken fat. Results are expressed as A415±SD; n=3. * indicates detection limit.

Figure 3:
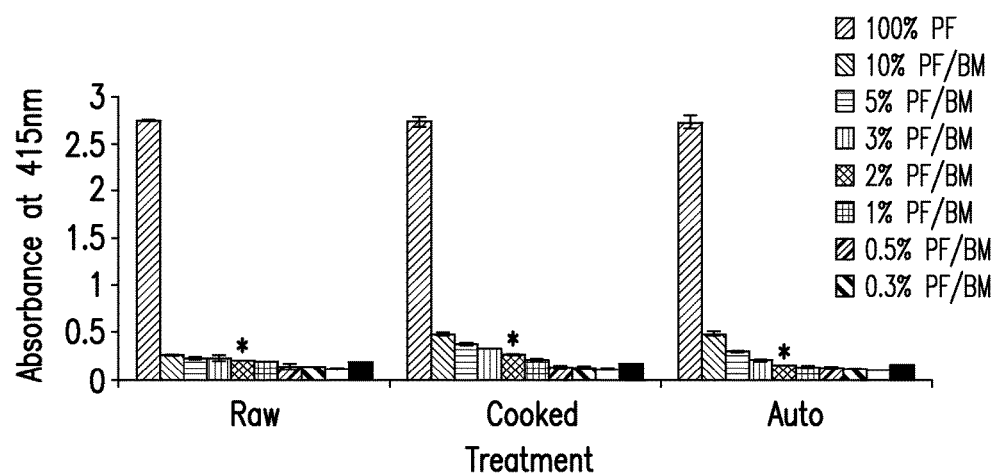
FIG. 3 shows bar graphs illustrating the detection limit of pork fat in raw, cooked and autoclaved beef meat using sandwich ELISA with purified MAb 8F10 as a capture antibody and biotin-conjugated MAb 5H9 as a detection antibody.

FIG. 3 shows the detection limit of pork fat in raw, cooked and autoclaved beef meat using sandwich ELISA with purified MAb 8F10 as the capture antibody and biotin-conjugated MAb 5149 as the detection antibody. Soluble proteins were extracted from pork fat in raw, cooked and autoclaved beef meat mixtures using 25 mL of PBS for raw, cooked and autoclaved samples, respectively. PF=pork fat; PF/BM=pork fat in beef meat; and BM=beef meat. Results are expressed as A415±SD; n=3. * indicates detection limit.

Figure 4:
FIG. 4 shows bar graphs illustrating the detection limit of pork fat in raw, cooked and autoclaved chicken meat using sandwich ELISA with purified MAb 8F10 as a capture antibody and biotin-conjugated MAb 5H9 as a detection antibody.

FIG. 4 shows the detection limit of pork fat in raw, cooked and autoclaved chicken meat using sandwich ELISA with purified MAb 8F10 as the capture antibody and biotin-conjugated MAb 5H9 as the detection antibody. Soluble proteins were extracted from pork fat in raw, cooked and autoclaved chicken meat mixtures using 25 mL of PBS for raw, cooked and autoclaved samples, respectively. PF=pork fat; PF/CM=pork fat in chicken meat; and CM=chicken meat. Results are expressed as A415±SD; n=3. * indicates detection limit.

Summarized results of the detection limits for the sandwich ELISA:
1. Pork fat in beef fat: raw: 1%; cooked: 2%; and autoclaved: 0.5%
2. Pork fat in chicken fat: raw: 0.3%; cooked: 0.5%; autoclaved: 0.5%
3. Pork fat in beef meat: raw: 2%; cooked: 2%; autoclaved: 2%
4. Pork fat in chicken meat: raw: 2%; cooked: 1%; autoclaved: 1%

Example 2

Detection of Pork Fat in Fat or Meat Mixtures Using Lateral Flow Assay

Sample protein extraction was performed in the same manner as described above, then laboratory mixed sample extracts are prepared as follows for the determination of the detection limit using a lateral flow test. The lateral flow assay strips are prepared using published procedures. To make sure the homogeneity of the sample extracts containing low levels of porcine fat proteins, artificially adulterated samples are prepared from 10% (w/w) adulterated sample extracts diluted by the extract of the matrix material as described below.
1. To 10% (w/w) pork fat in beef fat, pork fat in chicken fat, pork fat in beef meat, and pork fat in chicken meat adulterated sample extracts is added the appropriate amount of beef fat, chicken fat, beef meat and chicken meat extracts, respectively, to obtain 5% down to 0.3% (v/v) adulterated samples.
2. To 200 μL of the diluted samples in (1) above is added 100 μL, of diluent buffer (0.5% Triton X, 150 mM HCl, 50 mM Tris-HCl, pH 8.2) and the mixture heated in boiling water bath for 5 minutes.
3. The mixture is then allowed to cool for 2 minutes and then dispensed (approximately 150 μL) unto the dipstick slowly in a drop-wise fashion and color developed for 15 to 30 minutes.

Results

Table 2 shows that the detection of pork fat in fat or pork fat in meat mixtures can be achieved at low levels (<1%) using a lateral flow rapid test, regardless of whether the sample is raw, cooked or autoclaved. In the case of pork fat in chicken fat raw, although adulteration levels below 0.3% are not tested, judging from the intensity of the positive band obtained for 0.3% pork fat in chicken fat raw, the detection limit may be even lower than 0.3%. Table 2 shows the detection limits for pork fat detection using a lateral flow strip test.

TABLE 2

| Sample | Treatment | Detection limit (v/v) |
| --- | --- | --- |
| Pork fat in beef fat | Raw | 0.3% |
|  | Cooked | 0.3% |
|  | Autoclaved | 0.5% |
| Pork fat in chicken fat | Raw | 0.3% |
|  | Cooked | 0.3% |
|  | Autoclaved | 0.5% |
| Pork fat in beef meat | Raw | 1% |
|  | Cooked | 1% |
|  | Autoclaved | 1% |
| Pork fat in chicken meat | Raw | 1% |
|  | Cooked | 1% |
|  | Autoclaved | 1% |

REFERENCES

The following references are referred to above and/or describe technology that may be used with the present invention and are incorporated herein by reference:

1. O. Abbas, J. A. F. Pierna, R. Codony, C. von Holst, and V. Baeten, "Assessment of the discrimination of animal fat by FT-Raman spectroscopy," *J. Mol. Struct.* 924-26: 294-300 (2009).
2. M. Ahmed, M. J. Neville, M. J. Edelmann, B. M. Kessler, and F. Karpe, "Proteomic analysis of human adipose tissue after rosiglitazone treatment shows coordinated changes to promote glucose uptake," *Obesity* (Silver Spring) 18(1):27-34 (2010).
3. A. A. Aida, Y. B. C. Man, C. M. Wong, A. R. Raha, and R. Son, "Analysis of raw meats and fats of pigs using polymerase chain reaction for Halal authentication," *Meat Sci.* 69(1):47-52 (2005).
4. A. A. Aida, Y. B. C. Man, A. A. Hassan, A. R. Raha, and R. Son, "Specific polymerase chain reaction (PCR) analysis of raw meats and fats of pigs for halal authentication," *Middle East Journal of Scientific Research* 7(6):1008-13 (2011).
5. A. A. Aida, Y. B. C. Man, A. R. Raha, and R. Son, "Detection of pig derivatives in food products for halal authentication by polymerase chain reaction-restriction fragment length polymorphism," *J. Sci. Food Agr.* 87(4): 569-72 (2007).
6. S. Bellorini, S. Strathmann, V. Baeten, O. Fumiere, G. Berben, S. Tirendi, and C. von Holst, "Discriminating animal fats and their origins: assessing the potentials of Fourier transform infrared spectroscopy, gas chromatography, immunoassay and polymerase chain reaction techniques," *Anal. Bioanal. Chem.* 382(4):1073-83 (2005).
7. E. G. Bligh and W. J. Dyer, "A rapid method of total lipid extraction and purification," *Can. J. Biochem. Physiol.* 37(8):911-17 (1959).
8. S. Boulant, R. Montserret, R. G. Hope, M. Ratinier, P. Targett-Adams, J. P. Lavergne, F. Penin, and J. McLauchlan, "Structural determinants that target the hepatitis C virus core protein to lipid droplets," *J. Biol. Chem.* 281(31):22236-47 (2006).
9. C. L. Brennan, M. Hoenig, and D. C. Ferguson, "GLUT4 but not GLUT1 expression decreases early in the development of feline obesity," *Domest. Anim. Endocrin.* 26(4):291-301 (2004).
10. Y. B. C. Man, H. L. Gan, I. NorAini, S. A. H. Nazimah, and C. P. Tan, "Detection of lard adulteration in RBD palm olein using an electronic nose," *Food Chem.* 90(4): 829-35 (2005).
11. Y. B. C. Man, and M. E. S. Mirghani, "Detection of lard mixed with body fats of chicken, lamb, and cow by Fourier transform infrared spectroscopy," *Journal of the American Oil Chemists Society* 78(7):753-761 (2001).
12. Y. B. C. Man, Z. A. Syahariza, and A. Rohman, "Discriminant analysis of selected edible fats and oils and those in biscuit formulation using FTIR spectroscopy," *Food Anal. Methods* 4(3):404-09 (2011).
13. F-C. Chen, Y-H. P. Hsieh, and R. C. Bridgman, "Monoclonal antibodies to porcine thermal-stable muscle protein for detection of pork in raw and cooked meats," *J. Food Sci.* 63: 201-05 (1998)."
14. F-C. Chen, and Y-H. P. Hsieh, "Porcine troponin I: a thermostable species marker protein," *Meat Sci.* 61(1): 55-60 (2002).
15. F-C. Chen Y-H. P. Hsieh, R. C. Bridgman, "Monoclonal antibody-based sandwich enzyme-linked immunosorbent assay for sensitive detection of prohibited ruminant proteins in feedstuffs," *J. Food Prot.* 67:544-49 (2004).
16. Chernukha, "Comparative study of meat composition from various animal species," *International 56th Meat Industry Conference*. Tara, Serbia: technologija mesa, 167-71 (2011).
17. S. T. Chin, Y. B. C. Man, C. P. Tan, and D. M. Hashim, "Rapid Profiling of Animal-Derived Fatty Acids Using Fast GC×GC Coupled to Time-of-Flight Mass Spectrometry," *Journal of the American Oil Chemists Society* 86(10):949-58 (2009).
18. B. B. De Taeye, C. Christophe Morisseau, J. Coyle, J. W. Covington, A. Luria, J. Yang, S. B. Murphy, D. B. Friedman, B. B. Hammock, and D. E. Vaughan, "Expression and regulation of soluble epoxide hydrolase in adipose tissue, *Obesity* 18:489-498 (2010).
19. P. Dugo, T. Kumm, A. Fazio, G. Dugo, and L. Mondello, "Determination of beef tallow in lard through a multidimensional off-line non-aqueous reversed phase-argentation LC method coupled to mass spectrometry," *J. Sep. Sci.* 29(4):567-75 (2006).
20. ECSSC, *Opinion on the safety of tallow derivatives from cattle tallow* (1999).
21. B. Friguet, L. Djavadi-Ohaniance, J. Pages, A. Bussard, and M. Goldberg, "A convenient enzyme-linked immunosorbent assay for testing whether monoclonal antibodies recognize the same antigenic site. Application to hybridomas specific for the beta 2-subunit of *Escherichia coli* tryptophan synthase," *J. Immunol. Methods* 60:351-58 (1983).
22. G. Gondret, B. Guevel, E. Com, A. Vincent, and B. Lebret, "A comparison of subcutaneous adipose tissue proteomes in juvenile piglets with a contrasted adiposity underscored similarities with human obesity,"*J. Proteomics* 75(3):949-61 (2012).
23. K. Hiramoto, K. Kido, and K. Kikugawa, "DNA Breaking by Maillard Products of Glucose Amino-Acid Mixtures Formed in an Aqueous System," *J. Agr. Food Chem.* 42(3):689-94 (1994).
24. Y-H. P. Hsieh, F-C. Chen, and N. Djurdjevic, "Monoclonal antibodies against heat-treated muscle proteins for species identification and end-point cooking temperature determination of cooked meats," *Quality Attributes of Muscle Foods*. Xiong, Ho and Shahidi (eds.). Kluwer Academic/Plenum Publishers, N.Y. 287-306 (1999).
25. G. Iacobellis, D. Corradi, and A. M. Sharma, "Epicardial adipose tissue: anatomic, biomolecular and clinical relationships with the heart," *Nat. Clin. Pract. Cardiovasc. Med.* 2(10):536-43 (2005).

26. D. Indrasti, Y. B. C. Man, S. Mustafa, and D. M. Hashim, "Lard detection based on fatty acids profile using comprehensive gas chromatography hyphenated with time-of-flight mass spectrometry," *Food Chem.* 122(4):1273-77 (2010).
27. H-J. Jacobsen and R. Greiner, "Methods for detecting genetic manipulation in grain legumes," Jackson, J. F. & Linskens, H. F., editors. *Molecular methods of plant analysis: Testing for genetic manipulation in plants* New York: Springer, 64 (2002).
28. M. Kagawa, K. Matsubara, K. Kimura, H. Shiono, and Y. Fukui, "Species identification by the positional analysis of fatty acid composition in triacylglyceride of adipose and bone tissues," *Forensic. Sci. Int.* 79(3):215-26 (1996).
29. E. E. Kershaw, and J. S. Flier, "Adipose tissue as an endocrine organ," *J. Clin. Endocrinol. Metab.* 89, 2548-56 (2004).
30. H. A. Kuiper, "Summary report of the ILSI Europe workshop on detection methods for novel foods derived from genetically modified organisms," *Food Control* 10(6):339-49 (1999).
31. Lazarev, G. Smejkal, I. Romanovsky, A. Kwan, H. Cao, G. S. Hotamisligil, and A. R. Ivanov, "Proteomic analysis of murine adipose tissue using pressure cycling technology and high resolution tandem mass spectrometry," *US HUPO 3rd Annual Conference*, Seattle, Wash. (2007).
32. D. Lichtenberg, E. Opatowski and M. M. Kozlov, "Phase boundaries in mixtures of membrane-forming amphiphiles and micelle-forming amphiphiles," *Biochim. Biophys. Acta* 1508(12):1-19 (2000).
33. J. M. N. Marikkar, H. M. Ghazali, Y. B. C. Man and O. M. Lai, "The use of cooling and heating thermograms for monitoring of tallow, lard and chicken fat adulterations in canola oil," *Food Research International* 35 (10):1007-14 (2002).
34. J. M. N. Marikkar, H. M. Ghazali, Y. B. C. Man, T. S. G. Peiris and O. M. Lai, "Distinguishing lard from other animal fats in admixtures of some vegetable oils using liquid chromatographic data coupled with multivariate data analysis," *Food Chem.* 91(1):5-14 (2005).
35. M. S. Moawad, M. A. Tony and H. A. Aref, "Forensic identification of subcutaneous and perirenal adipose tissue samples in some farm animals using gas liquid chromatography," *Mansoura. Vet. Med. J.* XI(1): 13-20 (2009).
36. N. H. Mohan, B. C. Sarmah, M. K. Tamuli, A. Das, and K. M. Bujarbaruah, "Electrophoretic profile of porcine adipose tissue and a method for extraction of soluble proteins from fat tissue," *Indian J. Anim. Sci.* 77(12): 1248-50 (2007).
37. J. F. Montiel-Sosa, E. Ruiz-Pesini, J. Montoya, P. Roncales, M. J. Lopez-Perez, and A. Perez-Martos, "Direct and highly species-specific detection of pork meat and fat in meat products by PCR amplification of mitochondrial DNA," *J. Agric Food Chem.* 48(7):2829-32 (2000).
38. M. Motoyama, M. Ando M. K. Sasaki and H. O. Hamaguchi, "Differentiation of Animal Fats from Different Origins: Use of Polymorphic Features Detected by Raman Spectroscopy," *Appl. Spectrosc.* 64(11):1244-50 (2010).
39. H. R. Mottram, Z. M. Crossman, and R. P. Evershed, "Regiospecific characterisation of the triacylglycerols in animal fats using high performance liquid chromatography atmospheric pressure chemical ionisation mass spectrometry," *Analyst* 126(7):1018-1024 (2001).
40. D. J. Murphy, "The biogenesis and functions of lipid bodies in animals, plants and microorganisms," *Prog. Lipid Res.* 40(5):325-438 (2001).
41. G. Rastogi, M. S. Dharne, S. Walujkar, A. Kwnar, M. S. Patole, and Y. S. Shouche, "Species identification and authentication of tissues of animal origin using mitochondrial and nuclear markers," *Meat Sci.* 76(4):666-74 (2007).
42. Rohman and Y. B. C. Man, "FTIR spectroscopy combined with chemometrics for analysis of lard in the mixtures with body fats of lamb, cow, and chicken," *International Food Research Journal* 17(3):519-26 (2010).
43. Rohman, Y. B. C. Man, P. Hashim and A. Ismail, "FTIR spectroscopy combined with chemometrics for analysis of lard adulteration in some vegetable oils," *Journal of Food* 9(2):96-101 (2011).
44. Rosenow, T. N. Arrey, F. G. Bouwman, J. P. Noben, M. Wabitsch, E. C. M. Mariman, M. Karas, and J. Renes, "Identification of Novel Human Adipocyte Secreted Proteins by Using SGBS Cells," *J. Proteome Res.* 9(10): 5389-5401 (2010).
45. T. Sajic, G. Hopfgartner, I. Szanto, and E. Varesio, "Comparison of three detergent-free protein extraction protocols for white adipose tissue," *Anal. Biochem.* 415 (2):215-217.
46. Salgado-Somoza, E. Teijeira-Fernandez, A. L. Fernandez, J. R. Gonzalez-Juanatey, and S. Eiras, "Proteomic analysis of epicardial and subcutaneous adipose tissue reveals differences in proteins involved in oxidative stress," *Am. J. Physiol. Heart Circ. Physiol.* 299(1):H202-209 (2010).
47. M. Schreiner, R. G. Moreira and H. W. Hulan, "Positional distribution of fatty acids in egg yolk lipids," *J. Food Lipids* 13(1):36-56 (2006).
48. M. Seddon, P. Curnow and P. J. Booth, "Membrane proteins, lipids and detergents: not just a soap opera," *Biochim. Biophys. Acta* 1666(1-2): 105-117 (2004).
49. Sucipto, Irzaman, T. T. Irawadi, and A. M. Fauzi, "Potential of conductance measurement for lard detection," *International Journal of Basic and Applied Sciences* 11(5):26-30 (2011).
50. Szabó, H. Febel, L. Sugar, and R. Romvari, "Fatty acid regiodistribution analysis of divergent animal triacylglycerol samples—a possible approach for species differentiation," *Journal of Food Lipids* 14(1):62-77 (2007).
51. P. Trayhurn, C. A. Drevon and J. Eckel, "Secreted proteins from adipose tissue and skeletal muscle—adipokines, myokines and adipose/muscle cross-talk," *Arch. Physiol. Biochem.* 117(2):47-56 (2011).
52. L. Vaclavik, V. Hrbek, T. Cajka, B. A. Rohlik, P. Pipek, and J. Hajslova, "Authentication of animal fats using direct analysis in real time (DART) ionization-mass spectrometry and chemometric tools," *J. Agric. Food Chem.* 59(11):5919-26 (2011).
53. J. M. Wilkinson and R. J. Grand, "Comparison of amino acid sequence of troponin I from different striated muscles," *Nature* 271(5640):31-35 (1978).
54. J. D. Wood, R. I. Richardson, G. R. Nute, A. V. Fisher, M. M. Campo, E. Kasapidou, P. R. Sheard, and M. Enser, "Effects of fatty acids on meat quality: a review," *Meat Sci.* 66(1):21-32 (2004).
55. H. Yang, Z. Y. Xu, M. G. Lei, F. E. Li, C. Y. Deng, Y. Z. Xiong, and B. Zuo, "Association of 3 polymorphisms in porcine troponin I genes (TNNI1 and TNNI2) with meat quality traits," *J. Appl. Genet.* 51(1):51-57 (2010a).

56. H. Yang, Z. Xu, Z. Ma, Y. Xiong, C. Deng, and B. Zuo, "Molecular cloning and comparative characterization of the porcine troponin I family," *Anim. Biotechnol.* 21(1): 64-76 (2010b).
57. R. Zasadny and K. Kwiatek, "Validation study of a new procedure for measuring insoluble impurities in animal fat," *J. Anim. Feed Sci.* 15(2):337-44 (2006).
58. Y. T. Zhou, Z. W. Wang, M. Higa, C. B. Newgard, and R. H. Unger, "Reversing adipocyte differentiation: implications for treatment of obesity," *Proc. Natl. Acad. Sci. USA* 96(5):2391-95 (1999).

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method comprising:
    extracting proteins from an animal muscle-free adipose tissue sample with a phosphate buffered saline to form an aqueous protein extract comprising the phosphate buffered saline and soluble proteins extracted from the animal muscle-free adipose tissue sample by the phosphate buffered saline without homogenizing the muscle-free adipose tissue sample, and
    contacting the aqueous protein extract with a species-specific anti-troponin I monoclonal antibody to test whether the species-specific anti-troponin I monoclonal antibody binds to a protein in the aqueous protein extract,
    wherein the species-specific anti-troponin I monoclonal antibody is directly or indirectly conjugated to a label that shows the binding of the species-specific anti-troponin I monoclonal antibody with a species-specific troponin I, and
    wherein binding of the species-specific anti-troponin I monoclonal antibody to a protein in the aqueous protein extract indicates a presence of the species-specific troponin I in the animal muscle-free adipose tissue sample.
2. The method of claim 1, wherein the animal muscle-free adipose tissue is cooked.
3. The method of claim 1, wherein the animal muscle-free adipose tissue is raw.
4. The method of claim 1, wherein the animal muscle-free adipose tissue is autoclaved.
5. The method of claim 1, wherein the phosphate buffered saline is 10 mM phosphate buffered saline.
6. The method of claim 1, wherein a result of whether the species-specific anti-troponin I monoclonal antibody binds to a protein in the aqueous protein extract is displayed to a user on a visual display device.
7. The method of claim 1, wherein the species-specific anti-troponin I monoclonal antibody is a monoclonal antibody against porcine-specific troponin I, and wherein binding of the species-specific anti-troponin I monoclonal antibody to a protein in the aqueous protein extract indicates a presence of porcine-specific troponin I in the animal muscle-free adipose tissue.
8. The method of claim 1, wherein the species-specific anti-troponin I monoclonal antibody is a monoclonal antibody against poultry-specific troponin I, and wherein binding of the species-specific anti-troponin I monoclonal antibody to a protein in the aqueous protein extract indicates a presence of poultry-specific troponin I in the animal muscle-free adipose tissue.
9. The method of claim 1, wherein the species-specific anti-troponin I monoclonal antibody is a monoclonal antibody against ruminant-specific troponin I, and wherein binding of the species-specific anti-troponin I monoclonal antibody to a protein in the aqueous protein extract indicates a presence of ruminant-specific troponin I in the animal muscle-free adipose tissue.
10. The method of claim 1, wherein the species-specific anti-troponin I monoclonal antibody is a monoclonal antibody against bovine-specific troponin I, and wherein binding of the species-specific anti-troponin I monoclonal antibody to a protein in the aqueous protein extract indicates a presence of bovine-specific troponin I in the animal muscle-free adipose tissue.
11. The method of claim 1, wherein the species-specific anti-troponin I monoclonal antibody is a monoclonal antibody against sheep-specific troponin I, and wherein binding of the species-specific anti-troponin I monoclonal antibody to a protein in the aqueous protein extract indicates a presence of sheep-specific troponin I in the animal muscle-free adipose tissue.
12. The method of claim 1, wherein the animal muscle-free adipose tissue sample is a ground muscle-free adipose tissue.
13. The method of claim 12, wherein the ground muscle-free adipose tissue is a softened ground muscle-free adipose tissue, and
    wherein the softened ground muscle-free adipose tissue is produced by warming the ground muscle-free adipose tissue in an oven for 30 to 120 minutes at an oven heating temperature of 60 to 80° C.
14. The method of claim 13, wherein the oven heating temperature is 65° C.
15. The method of claim 13, wherein the method comprises:
    mixing the phosphate buffered saline and the softened ground muscle-free adipose tissue to form an extraction mixture containing fats from the softened ground muscle-free adipose tissue and an aqueous protein extract comprising the phosphate buffered saline and soluble proteins extracted from the softened ground muscle-free adipose tissue by the phosphate buffered saline.
16. The method of claim 15 comprising: shaking the extraction mixture at room temperature to fully mix the phosphate buffered saline and the softened ground muscle-free adipose tissue in the extraction mixture.
17. The method of claim 16 comprising: separating the aqueous protein extract from the extraction mixture.
18. The method of claim 16 comprising: centrifuging the extraction mixture after shaking at a reduced temperature for 15 to 60 minutes at a speed that is sufficient to form a solidified upper fat portion and a lower aqueous phase portion in the extraction mixture, and separating the lower aqueous phase portion from the extraction mixture by removing the solidified upper fat portion, wherein the solidified upper fat portion contains fats from the softened ground muscle-free adipose tissue, and wherein the lower aqueous phase portion contains the aqueous protein extract, wherein the reduced temperature is in a range from 1 to 10° C.

19. The method of claim 18, wherein the extraction mixture is sitting for at least 1 hour before centrifuging.

20. The method of claim 18, wherein centrifuging is conducted at 3220 g for 30 minutes at 4° C.

21. The method of claim 18 comprising: filtering the lower aqueous phase layer after removing the solidified upper fat portion to purify the aqueous protein extract contained in the lower aqueous phase portion.

22. The method of claim 21, wherein the lower aqueous phase portion is filtered through a filter paper.

23. The method of claim 1, wherein the method comprises: testing binding of the species-specific anti-troponin I monoclonal antibody binds to a protein in the aqueous protein extract via an immunoassay.

24. The method of claim 23, wherein the immunoassay is conducted by an automated instrument.

25. The method of claim 24, wherein the automated instrument comprises a computer.

26. The method of claim 23, wherein the immunoassay comprises a Western blot assay, and wherein the binding of a species-specific troponin I in the aqueous protein extract is tested with more than one species-specific anti-troponin I monoclonal antibodies that recognize troponin I from different species.

27. The method of claim 23, wherein the immunoassay comprises a lateral flow assay.

28. The method of claim 23, wherein the immunoassay comprises an enzyme-linked immunosorbent assay.

* * * * *